United States Patent [19]

Banko

[11] 4,019,514
[45] Apr. 26, 1977

[54] SURGICAL SYSTEM FOR CONTROLLING THE INFUSION OF FLUID TO AND THE EVACUATION OF FLUID AND MATERIAL FROM AN OPERATING FIELD

[75] Inventor: Anton Banko, Bronx, N.Y.

[73] Assignee: Surgical Design Corporation, Long Island City, N.Y.

[22] Filed: Nov. 17, 1975

[21] Appl. No.: 632,768

Related U.S. Application Data

[63] Continuation-in-part of Ser. No. 475,398, June 3, 1974, Pat. No. 3,920,014.

[52] U.S. Cl. .............................. 128/230; 128/276
[51] Int. Cl.² .......................................... A61M 1/00
[58] Field of Search .......... 128/230, 276, 277, 278, 128/2 A; 137/205

[56] References Cited
UNITED STATES PATENTS

| 2,646,042 | 7/1953 | Hu | 128/276 X |
| 3,429,313 | 2/1969 | Romanelli | 128/230 X |
| 3,513,846 | 5/1970 | Gallo | 128/276 X |
| 3,599,639 | 8/1971 | Spotz | 128/276 |
| 3,788,305 | 1/1974 | Schreiber | 128/276 X |
| 3,812,855 | 5/1974 | Banko | 128/276 X |
| 3,920,014 | 11/1975 | Banko | 128/230 |

Primary Examiner—John D. Yasko
Attorney, Agent, or Firm—Darby & Darby

[57] ABSTRACT

A system for controlling the infusion of fluid to an operating field at a selected predetermined and programmed pressure, as a counterpart to an instrument for severing material from an object in the field, and for evacuating the severed material from the field in a suspension or emulsion of the infusion fluid. The system includes a simplified fluid flow control system for changing the pressure of the infusion fluid flow into the operating field during different modes of operation of the system.

10 Claims, 3 Drawing Figures

SURGICAL SYSTEM FOR CONTROLLING THE INFUSION OF FLUID TO AND THE EVACUATION OF FLUID AND MATERIAL FROM AN OPERATING FIELD

This application is a continuation-in-part of my prior copending application Ser. No. 475,398 filed June 3, 1974 entitled "SURGICAL SYSTEM FOR CONTROLLING THE INFUSION OF FLUID TO AND THE EVACUATION OF FLUID AND MATERIAL FROM AN OPERATING FIELD" now U.S. Pat. No. 3,920,014 granted Nov. 18, 1975.

This invention relates to a surgical apparatus and more particularly to an apparatus having particular utility in an operation taking place in a closed operating field, such as the eye of an animal or human being.

In my aforesaid patent, a system is disclosed for use in conjunction with a surgical instrument of the type which can remove material from an object, such as by cutting, drilling, emulsifying such as by using ultrasonic energy, tearing, etc. The system operates to infuse fluid in an operating field for certain purposes, such as to maintain a predetermined pressure, and also for evacuating from the field the severed material removed from the object in suspension with or as an emulsion of the infusion fluid. The system of the aforesaid patent is also capable of performing a variety of functions all under the control of an operator. Among these are supply of a fluid to the operating field at a selected predetermined pressure after the surgical instrument is inserted to keep the operating field, for example the eye, formed in its normal physical shape both before and during the operation. During the operation the system also: (1) creates an evacuation flow for transportation of the material severed by the surgical instrument, which material is suspended or is emulsified in the supplied fluid and in the normal fluid of the operating field; (2) substitutes fluid to compensate for the volume of material, both solid and liquid, removed from the operating field; and (3) maintains the pressure in the operating field within workable and safe tolerance levels.

The system of the prior patent also operates to generate a reverse flow of fluid through the instrument into an operative portion thereof when tissue in the proximity of or in an evacuation opening is to be pushed away or material being removed inadvertently has entered the instrument and has to be moved back into the operating field. As a safety feature, it also builds up a pressure in the evacuation line at or close to the level of the pressure in the operating field when the evacuation process has been stopped to substantially prevent further motion of material from the operating field into the instrument. This prevents the operating field from being emptied of material which would ultimately cause it to collapse. In addition, the system controls the operation of a cutting or emulsifying means to be either: in a ready condition; in an operative condition during the conduct of the operation; or, in the case where a movable cutter is used, to move the cutter in the reverse direction during the application of fluid in the reverse mode.

The present invention relates to an improvement over the system of the prior patent with respect to a simplified arrangement for controlling the pressure of the infusion fluid as the system goes from a "ready" mode to an "operating" mode and/or "reverse" mode wherein material is removed. In accordance with the invention, a control system is used which operates on a pressure control valve in the line pressurizing the container with infusion fluid to change the fluid pressure during the three modes. This compensates for a pressure drop which occurs when the system switches from the ready to the operating mode. At due to constant hydrostatic pressure in the infusion line, pressure in the line would drop proportional to the evacuation.

It is therefore an object of the present invention to provide a novel surgical system for controlling the infusion of fluid to an operating field, the rate of separation or cutting of material from the object being operated on, and the evacuation of fluid and material from the operating field.

A further object is to provide a liquid infusion and material evacuating system for use in connection with a surgical instrument for removing material from an object.

An additional object is to provide a system utilizing easily operated control members for controlling the infusion of fluid and the evacuation of fluid and material from an operating field.

Another object is to provide a liquid infusion and material evacuating system for use with a surgical instrument in which safety features are provided to prevent an unsafe overpressure or an underpressure condition.

Another object is to provide a liquid infusion and material evacuating system for use with a surgical instrument in which the pressure of the infusion fluid supply is controlled as the instrument is switched from one mode of operation to another.

Other objects and advantages of the present invention will become more apparent upon reference to the following specification and annexed drawings, in which.

Figure 1:
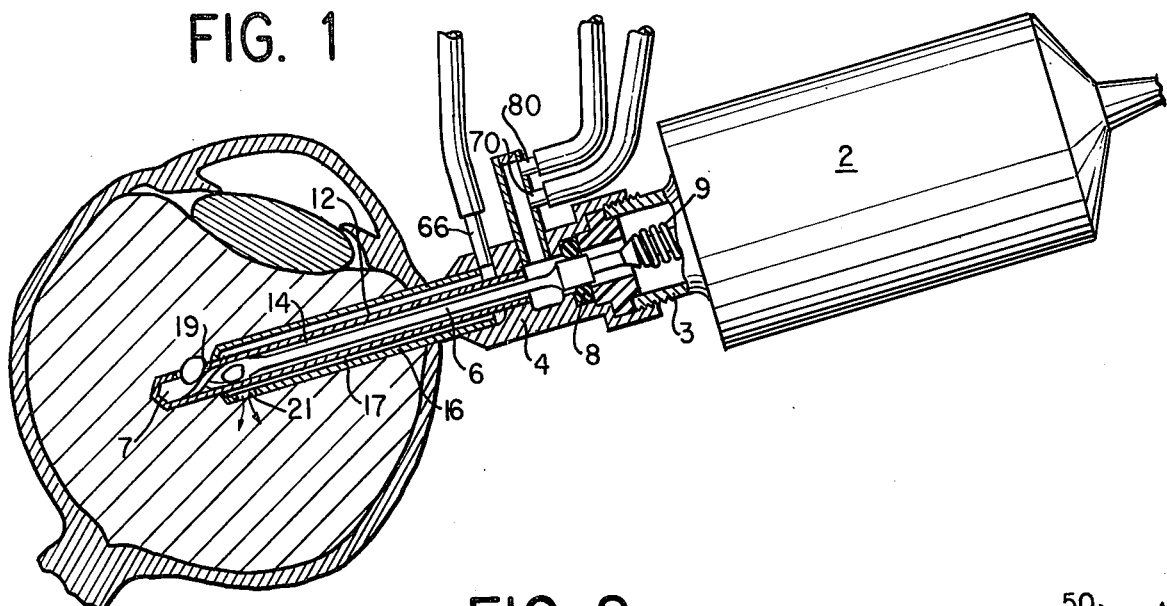
FIG. 1 is an overall plan view, taken partly in cross-section, of a typical instrument for use with the system of the present invention.

Referring to the drawings, the system is described with respect to performing an operation on the eye of an animal or a human being. It should be understood, of course, that the system can be utilized in the performance of other types of operations and in other types of environments.

FIG. 1 shows a typical surgical instrument 10 which can be used with the control. It should be understood, however, that the system can be used with any type of instrument or instrument set-up which requires pressurized flow of a liquid (infusion) and/or evacuation of fluid and severed material from an operating field. This includes various types of mechanical cutting instruments as well as other instruments, for example those of the ultrasonic type, which emulsify material to be removed.

In the embodiment of the invention being described, the tip of instrument 10 is shown as having pierced through a section of the eye, for example after an incision has been made. The tip of the instrument is shown in the vitreous of the eye to remove tissue therefrom or to treat the eye. The instrument of FIG. 1 also can be used to remove material from other parts of the eye such as the lens or iris. It should be understood that the system can be used with any compatible type of instrument to perform operations or treatment in any portion of the body of a mammal.

The instrument 10 of FIG. 1 includes an electric motor 2, preferably of the reversible type, from which extends a collar 3. A fitting 4 is screwed onto collar 3 and concentric inner and outer tubular members 12 and 16 entend from fitting 4. Inner tube 12 defines a central passage 14 through which evacuation takes place over a line 80, to be described below, which communicates with passage 14 through a coupling on fitting 4. The space between the inner and the outer tubes 12 and 16 defines a passage 17 through which infusion fluid is supplied over a line 66 and reverse flow fluid over a line 70, both of which lines are described below. Lines 80 and 70 communicate with passage 17 through a common coupling in fitting 4.

The inner, evacuation flow, passage 14 of the instrument has an opening 19 at the end thereof through which the evacuation flow takes place from the operating field. The infusion flow member 16 has one or more openings 21 in its wall, spaced from and opposite to opening 19 to avoid interference, through which fluid is injected into the operating field. A shaft 6 having a fluted cutter 7 at the end thereof is located in the inner passage 14. The shaft is connected to the motor output shaft and rotates in bearing and sealing elements 8 in the fitting 4 so that the cutter will translate across and coact, preferably without clearance, with the opening 19 to produce a shearing action. Shaft 6 is preferably biased by a spring 9 so that the cutter 7 will coact with the surface surrounding the evacuation opening 19 to produce a shearing action to cut any tissue therebetween. In operation, the tip of the instrument is moved to place the evacuation opening 19 at the site of the material to be severed. The evacuation flow from opening 19 aids in drawing the material into a relationship so that it can be severed by the moving edge of cutter 7 and the edge of opening 19. The severed material, in suspension or as part of an emulsion, is drawn up passage 14 and is removed via passage 14. Infusion fluid is supplied over line 66 to the eye through passage 17 and its opening 21.

The system of the invention regulates the flow of infusion fluid to provide a selected predetermined pressure in the eye. In addition it maintains the evacuation flow rate to within predetermined safe limits. This is described below.

Figure 2:
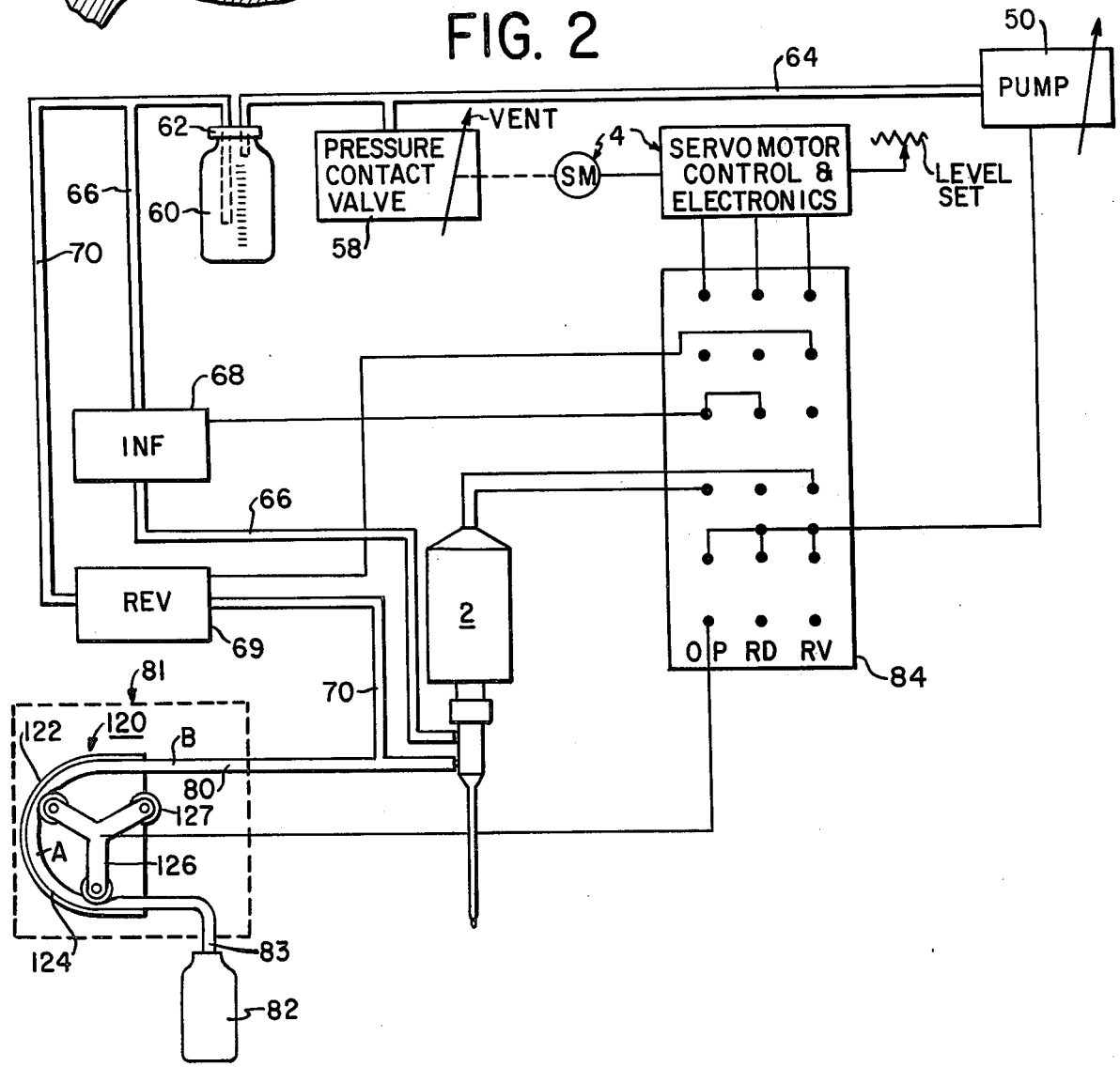
FIG. 2 is a schematic line diagram showing the various components of the system and their operation, with particular emphasis on the fluid flow portions of the system and their various components.
Figure 3:
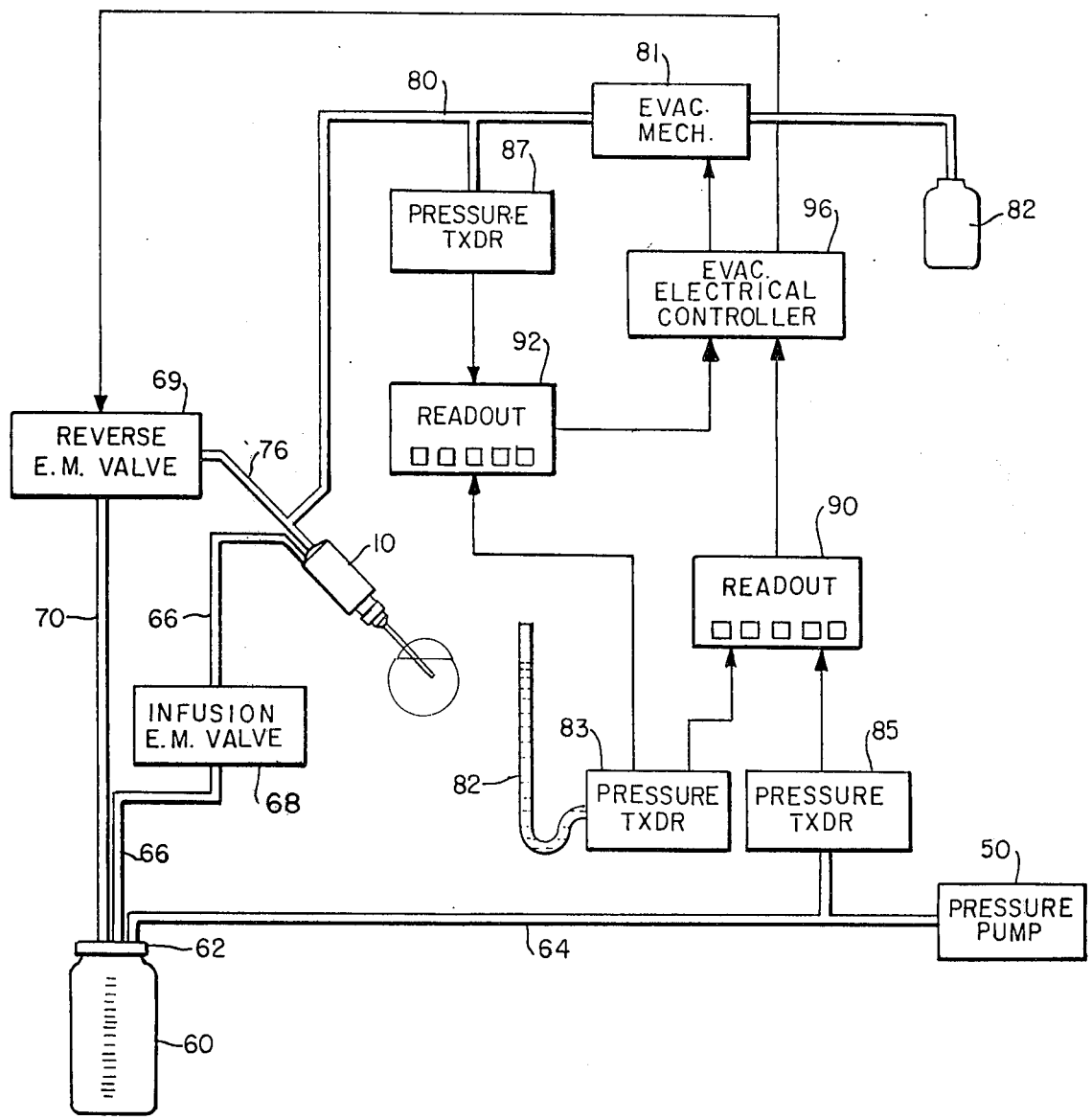
FIG. 3 is a schematic diagram of the system particularly illustrating the electronic control function.

FIGS. 2 and 3, taken together show the fluid flow and electronic control system components of the system. In these figures, the double lines indicate fluid flow paths and the single lines electrical connections. The infusion fluid supply for the instrument 10 is illustratively shown as a bottle 60 having a calibrated scale thereon. In a typical case, saline solution is utilized as the fluid. The bottle 60 is capped at 62 so that it can be pressurized over a line 64 which extends into the bottle. The line 64 can be of any conventional type of tubing, for example, vinyl tubing, and it is connected to a compressor, or pump, 50. Pump 50 is any suitable type producing an air flow. The air entering the infusion bottle is preferably filtered by a suitable filtering means (now shown) to make it sterile. The pump 50, in conjunction with various regulating valves, produce a different constant pressure during different operating modes in line 64 and bottle 60 within selectable, relatively well defined limits, which can be pre-set.

An infusion line 66 also extends into the bottle 60 to receive fluid therefrom to be conveyed to the outer passage 17 of the instrument 10. This is the infusion fluid to such passage. An electromechanically controlled valve 68 is located in line 66 between bottle 60 and the instrument to control the fluid flow. Line 66 also can be of vinyl or other suitable material.

A second fluid line 70 also receives fluid from the bottle 60. This is the reverse and suction release fluid-flow line whose outlet end is connected to the instrument 10 to supply fluid to the inner passage 14 of the instrument. An electromechanically operated valve 69 is located in line 70 between the bottle 60 and the outlet of reverse flow line 70 to control the flow of fluid to the outlet.

An evacuation mechanism 81 removes the severed or emulsified material from the eye through an evacuation line 80 which is connected to the inner passage of the instrument 10. The evacuation is carried out at a substantially constant rate, which can be selected and preset, to create a flow of material from the eye in a substantially gasless column of liquid. The evacuation mechanism preferably includes a peristaltic type pump, for example, the Master Flex Tubing Pump, Model 7013 made by Cole-Parmer Company, of Chicago, Ill. The operation of this type of pump is described in greater detail below. Line 80 empties into a waste bottle 82 through the pump and a line 83. The material emptied into bottle 82 includes fluid from the operating field together with the material severed from the object by the instrument.

Solenoid operated, pressure regulating valve 58 is provided in the pressure line 64 to the bottle 60. It has a servomechanism 4 pressure set adjustment, indicated by the arrow, to control or set the pressure in line 64 to the bottle and also to the instrument. Valve 58 is a multi-turn valve with a moving piston which determines an opening for leakage into the atmosphere. As described below, the pressure set adjustment of valve 58 is controlled by a servomotor and it control mechanism.

Valve 58 controls the pressure in the infusion line 66 or the reverse flow line 70 during both the "ready" ($P_{RD}$), the operate ($P_{OP}$) or the reverse ($P_{RV}$) modes of the system. The ready mode pressure $P_{RD}$ is the lowest pressure of the system. When valve 58 is operating during the ready mode, the infusion line control valve 68 is open and the reverse flow line control valve 69 is closed. During the operating mode, valve 58 is operated by the servomechanism to set the $P_{OP}$ pressure in line 66 to be higher than it is when in the ready mode. During the "operating" mode the infusion line control valve 68 is open and the reverse flow line control valve 69 is closed. The valve is initially set up to produce pressure in line 66 needed for the ready mode $P_{RD}$. On switching to the operate mode, the valve is closed somewhat by the servomechanism to raise the pressure in line 66 to $P_{OP}$ to a value proportional to the evacuation rate. On switching back to the ready mode, the servomechanism opens valve 58 to reduce the pressure in line 66 to $P_{RD}$.

The servosystem closes valve 58 to set the pressure ($P_{RV}$) in the reverse flow line 70 during the "reverse" mode, for example at a value of 7–10 mm Hg above that of the ready mode. During reverse flow, the infusion control valve 68 is closed and the reverse line control valve 69 is open. As indicated above:

$P_{RD} < P_{RV}$ and $P_{OP}$ is equal to $P_{RD} \times K$ (evacuation flow rate), where $K$ is a constant corresponding to the resistance to flow through the infusion line and the evacuation flow rate is in cc/min.

Each of the valves 68 and 69 is of conventional construction and is operable to an open or a closed condition by a control circuit generally indicated at 84. The electric signals from the control circuit 84 are transmitted over signal lines, illustrated by the single lines, to the various valves to open and close them and to the servomotor. The servomotor position is also determined by the potentiometer determining the evacuation rate. In FIG. 2 the circuit 84 is illustrated in the form of a multi-deck switch. The three control portions are Operate on the left, Ready in the center, and Reverse to the right. The single lines back to the switch indicate that the particular component is energized. The switch can be a foot switch which has three positions corresponding to the ready, operate and reverse modes. The ready mode can be a neutral, or middle, position of the foot switch; operate the forward position and reverse the rear position.

FIG. 3 illustrates additional details of the electronic control system as well as additional components of the fluid control system. In FIG. 3, the level of fluid in a tracking tube 82 is located physically above the level of fluid in the supply bottle 60. The tracking tube 82 is essentially a manometer and can be mounted, for example, on a ring stand. The level of the fluid in the long arm of the tracking tube, which for example can be water, is set to the level of the eye being operated upon. The tracking tube pressure level is communicated to the servosystem to adjust the pressure in the infusion line 66, and the reverse flow line 70. It also corrects the reading of pressure in the evacuation line 80. It is used to calibrate the pressure in these lines to a base, or reference, pressure. As described below, this is used to avoid excessive high or low pressure in either of these lines.

A pressure transducer 83 of any suitable conventional type is connected to the tracking tube 82. Transducer 83 converts the pressure in tracking tube 82 to an electrical output signal which is conveyed to an electronic circuit commanding the servosystem to correct the pressure considering the new base point. A digital readout device 90 is calibrated to visually display an adjustable set pressure in terms of mm of Hg. Any conventional readout device can be used, for example, one of the digital voltmeter type, made by Data Technology Corp. of Santa Anna, Calif., Model 3212-02. Readout 90 will display a reading set by a pressure setting potentiometer and a signal from a second transducer 85, which is connected in pressure line 64, may or may not affect the reading. Readout 90 may or may not be wired to display the difference between the two signals from transducers 85 and 83. Its display represents the infusion pressure at the operating site which should be kept at a set level regardless of the evacuation rate. This is close to the actual pressure of the infusion fluid supplied to the eye. The output signal representative of this displayed pressure difference is also available at the output of readout 90 as an electrical signal.

The pressure above that in the bottle 60 which is required to raise the liquid level in the infusion line 66 and/or reverse flow line 70 to the level of the liquid in the tracking tube, which is at the same level as the eye physically, can be indicated on readout 90 as the starting pressure, or zero. This is so when the liquid in the bottle 60 is at the designated height, which is usually at a nominal 1,000 cc level. When the level of fluid in the bottle drops, the reading of the readout 90 is excessive for the amount of drop of level (a given amount of millimeters of Hg) and the servomotor can compensate for this drop as well.

Any raising, or lowering, of the pressure in the bottle 60 or the pressure line 64 will raise, or lower, the level of the liquid in the infusion line 66 and the reverse flow line 70 and increase, or decrease, the pressure in the eye. During a typical operation, the amount of fluid used from the bottle 60 is relatively small so that the change in pressures caused by this is minimal.

A pressure sensor 87 is also located in the evacuation flow line 80 to sense the pressure in the line and to produce an electrical signal representative of it. This signal is supplied to a second readout device 92 which also receives a signal from the tracking pressure transducer 83. Device 92 displays in digital form, calibrated in millimeters of Hg, the difference between the pressure in line 80 and the tracking tube pressure. That is, the readout of device 92 is the evacuation flow pressure referenced to the tracking pressure. An electrical signal representative of the latter pressure is present at the output of readout 92.

The evacuation mechanism 81 is to be operated to maintain a constant evacuation flow in line 80. As indicated previously, the mechanism includes a constant displacement type pump, which in the preferred embodiment is a peristaltic pump 120 (FIG. 2). This has a hemispherical housing portion 122 of rigid material and a flexible plastic tubing 124 within the housing against which a triple arm roller system 126 rotates. The rollers 127 are spaced about 120° apart. The roller system 126 is rotated by a suitable motor (not shown) whose speed can be controlled. The inlet to pump 120 is the evacuation line 80 which is preferably a rigid plastic tubing. The outlet 83 of the pump is to the waste bottle 82.

The peristaltic pump 120 moves a column of liquid in a section A between two of its rollers 127, creating space for the contents of section B in tubing 80 between the instrument outlet and the closest roller 127 of pump 120 to the instrument. Rotation of the roller on the tubing in the pump 120 in area A creates a flow of material out of the pump exit passage 83. Fluid is being forced into the operating field at the same time over the infusion line and up to the pump inlet.

When the persistaltic pump inlet is near the eye and the instrument is connected to the pump by a relatively short and rigid tube 80, then the displacement of fluid by the pump is communicated to the eye with negligible time delay imposed by a flow through the cutting opening 19 of the instrument.

The system operates in several distinct modes which are described below:

1. Ready Mode — To produce this mode of operation the instrument is turned on and the electrical circuitry is such that the motor for the cutter of instrument 10 is off and the cutter does not rotate. Evacuation mechanism 81 is off but pressure pump 50 is operating. At the same time, valve 58 in the pressure line 64 is open. The infusion line control valve 68 is open and the reverse pressure line control valve 69 is closed. The valve 69 also is controlled to open after the evacuation process is started by the surgeon and pressure in the evacuation line drops below a preset value. The valve closes by a signal from transducer 85, after the pressure in the evacuation line is close to or reaches the pressure in the eye.

In this mode the pressure of the infusion fluid in line 66 is most limited and is being produced only to maintain the pressure in the operating field and to compensate for any leakage through the incision in the operating field and the instrument. The adjustment of valve 58 is initially set to produce this pressure $P_{RD}$. This pressure is normally something above the pressure level in the tracking tube, in the order of 15–30 mm of Hg above zero in a typical case of the example being described. In general, there is a small pressure drop in the infusion line 66 between bottle 60 and the instrument. In the ready mode, the pressure in the evacuation line 80, as indicated on readout 92 is equal to the pressure in the infusion line, except for pressure drops in lines lines 66 and 80, as indicated by the readout 90, since control valve 68 is open and valve 69 is controlled to be closed. At the same time, the pressure regulating valve 58 is open and at pressure $P_{RD}$, thereby producing the same pressure in both lines 66 and 80 at the operating site, through the fluid connection within the operating site provided by the infusion and the evacuation ports of the instrument.

In an alternative mode of operation (not shown in the diagram), both valves 68 and 69 can be opened in the ready mode. When this occurs, the infusion fluid is supplied over line 70. When both valves 68 and 69 are open the pressure in the eye rapidly builds to the proper level to keep it formed. This arrangement is useful when the instrument is first turned on so that line 80 will fill up with fluid.

In either arrangement, in a typical case of the ready mode, at the evacuation passage of the instrument, where the eye is being operated on through an incision which is closed so that the eye itself is essentially fluid-tight, the pressure $P_{RD}$ is set at about 15–20 mm of Hg above atmospheric pressure. In an "open sky" operation, where the eye is open to the atmosphere, the pressure is kept at zero, or slightly above, to prevent outflow of material from the eye. A manually controlled switch (not shown) is also provided, to close both control valves 68 and 69 after lines 66 and 80 are filled with fluid. This prevents any movement of fluid into or out of the instrument which is especially useful during an open sky type operation.

2. Operating Mode — This mode is obtained by having the operator of the system operate the foot switch, for example to the forward position. This completes electric circuits to keep on the pressure pump 50 turn on, the evacuation mechanism 81 and to operate the instrument's electric motor to turn the cutter in the forward direction. Where other types of instruments are used, for example an ultrasonic probe or turbofragmentator, these would be energized at this time. Reverse flow line control valve 69 is closed and infusion line control valve 68 is opened.

The servosystem now operates to adjust valve 58 to produce a slightly higher pressure in line 66. This is done because there is a pressure drop, usually in the order of about 3,5 mm Hg for removal of each cc/min of material, and it is desired to maintain a stable condition in the operating field.

As described previously, the rate of infusion fluid flow depends on the rate of evacuation. The maximum incoming rate of infusion fluid is limited so as not to create prohibitive streaming and consequent undesired displacement of floating tissue and other substances in the operating field, generally near and around the cutting opening 19 of the instrument 10. A high velocity of the incoming infusion liquid is desirably avoided since it has a mass impulse which may damage delicate tissue in the operating field.

The pressure in the operating field is to be maintained within tolerable limits below a desired maximum level, usually less than 30–35 mm of Hg above the atmospheric pressure in the case of a normal operation on the eye. However, for example, in the case where there is bleeding in the eye, the pressure can be set to control the bleeding by increasing it to counteract the pressure of the blood being pumped by the heart. The evacuation system will also operate at this higher pressure to remove the blood from the operating site permitting better visualization for cauterizing if bleeding does not stop spontaneously. After the latter is done, the pressure is reduced and the operation continued at the lower pressure. Therefore, the maximum rate of inflow of the infusion fluid must be controlled and, in some cases, limited. To accomplish this the evacuating system will not permit the evacuation to exceed a rate at which the pressure in the operating field can be maintained without creating undesirably high inflow rates of the infusion fluid.

During the operating mode the material separated by the instrument cutter is entrained in suspension in the infusion fluid and is moved to the waste bottle 83 by the evacuation mechanism 81. The operating pressure in the infusion line is established by valve 58. The pressure in the evacuation line 80 depends on several factors. These are: (1) the cross section of the inlet opening to the instrument, this changes where there is a movable cutter; (2) the speed of the evacuation mechanism itself; and (3) the viscosity of the infusion fluid and the material being removed.

The pump 120 is normally set to rotate at a constant speed to create a desired flow rate to fluid through the eye. The flow resistance through the instrument opening 19 and the rest of the evacuation line 80 is changing continuously during the operation. When the resistance increases, a greater force is needed to move a slightly smaller amount of suspension by the pump (the tube 80 shrinks and volume A slightly decreases due to a lower pressure in portion B of the line). The flow rate decreases slightly through the instrument cutter openings as well. This occurs as the volume of portion B of the line 80 decreases (tubing shrinks) due to lower pressure inside generated by increased resistance at the instrument opening.

When the resistance at the opening 19 increases further and the pump is still moving at a set speed, evacuating the fluid suspension from volume B, the pressure in volume B decreases further. If this process continues the column of liquid in portion B of the tubing will break and form spaces of low pressure vapors or even vacuum. If there is any air or other gases dissolved in the suspension, they will start to separate and their volume will increase as the pressure in volume B drops further.

So far no damage was done to the eye. Exit of the infusion solution is blocked, the eye is formed and its inside pressure is at its maximum desired level. If the resistance at the instrument opening would decrease slowly and gradually, which seldom happens, then the flow from the eye will resume and increase gradually until volume B is filled up again. The outflow from the eye is matched by the inflow so the eye stays formed. The flow will then stabilize at a slightly changing level. In a more typical case, the resistance decreases momentarily, e.g. because the instrument evacuation opening 19 is unblocked, and the volume B, which was partially or totally empty, fills up in a short time. The flow out of the eye is then greater than the infusion fluid flow into the eye. The eye loses its desired pressure and it will soften and collapse. Also, portions of healthy tissue of the eye may enter the cutter opening of the instrument with disastrous effects.

To prevent this from occurring with the described system, it is imperative to prevent prohibitive reduction of volume or density of the fluid suspension in volume B of the evacuation line 80. This is achieved by keeping B small and its inside pressure relatively high. Short tubings with a small inner diameter will provide the small volume. The change in volume in relation to the original volume will be small if the tubing is made of rigid material (metal, or thick wall flexible plastic tubing, for example, TYGON).

When the critical pressure (at which cohesive forces in the liquid column are exceeded) is reached, the liquid column will break and liquid-less spaces can be noticed through the wall of a clear flexible plastic tubing. The pressure level at which this separation takes place depends on the consistency of the liquid suspension and its temperature, but it can be clearly established for a given case. This pressure level can be observed on a pressure (suction) gauge and the pump can be stopped before it reaches the undesired level. The liquid column will not break and gases will not separate if pressure in volume B is kept above a given level. This may be achieved by stopping the pump prior the critical pressure is reached.

Separation of gases from the liquid suspension is a third disturbing factor (the first, shrinkage of tubing, the second, breakage of liquid column). Gases dissolved in liquid can be separated at a given (room) temperature if pressure on and in the liquid is decreased. As before, when pressure in a clear elastic plastic tubing is sufficiently reduced, at first a small quantity of very small gas bubbles appear in the liquid and as pressure if further reduced the number and size of the bubbles increases. The pressure at which the separation starts to be apparent can be observed on a pressure gauge and if the pump is stopped before the pressure reaches the undesired value, the separation will not occur. If some small degree of separation occurs it will not be harmful in terms of the problem described.

In either case of breaking of the column or fluid or separation of gases, pump 81 can be stopped manually if and when the observed conditions in portion of the line B visually appear to become critical. Pump 120 also can be stopped automatically, for example, pressure transducer 87 regulates the pressure in line 80. The transducer 87 produces a signal which is supplied to control circuit 96. If the pressure in line 80 falls below a predetermined minimum value, which can be selected and preset into the evacuation control circuit 96, the latter circuit produces an output signal which shuts off mechanism 81. In a typical embodiment of the invention, this is designed to occur when the pressure in evacuation line 80 is at between about 150 to 760 mm of Hg below atmosphereic pressure. This is a safety feature of the system.

When, and if, the flow from the eye through the cutter opening 19 of the instrument resumes (or increases) the pressure in volume B will increase and the pump can be started again, manually or automatically. In the latter case, the evacuation control circuit produces an output signal in response to the pressure sensed by transducer 82 to start the mechanism 81 again. A 10% pressure margin between OFF and ON has been found to be satisfactory.

If flow of liquid from the eye stops, or is reduced due to the blockage of evacuation port 19, or the viscosity of the tissue, entering the port 19 is increased, then the pressure in line 80 drops and transducer 87 triggers the control circuit 96 to stop mechanism 81. The pump 120 is stopped and since the portion B of line 80 is not occupied by expanding or compressive spaces which are empty or filled up with rarefactored gases, the flow from the eye will stop soon after the pump is stopped. The delay time depends on the difference in pressure in line 80 and in the eye, since the shrinkage of volume B depends on the magnitude of this differential pressure. When the pump is stopped and flow continues out of the eye until the pressure in the eye is equalized with the pressure in line B.

In order to prevent a flow of liquid from the eye after the pump is stopped, liquid should be brought in portion B of line 80 from the reverse flow line 70 until equilibrium is acheived between pressure in the eye and pressure in portion B. This can be done by opening the reverse flow control valve 69 when the evacuation process is stopped. Valve 69 is normally closed during the evacuation process.

As an alternative the pump 120 could be turned in the opposite direction to deliver liquid and increase the pressure in portion B of line 80 until equilibrium between the pressure in the eye and the pressure in portion B is achieved. Turning of the pump in the opposite direction can be accomplished by operating a specific switch by hand and keeping the pump running until the observed pressure reaches a specific value on a pressure gauge in line 80. It also can be done automatically as the pump is being de-energized from providing fluid flow from the eye it can be energized to produce a reverse flow until a predetermined value of pressure of equilibrium between pressure in the eye and pressure in portion B of line 80 is reached. The reverse flow into portion B of evacuation line 80 after the evacuation process is stopped by the surgeon is produced by a fixed or adjustable pressure in the bottle 60 until the pressure in the portion B has reached a desired fixed or adjustable value. This is determined by the transducer 87 and circuit control 96. As another alternative, when the operation is being performed in an open eye, the adjusted or adjustable flow is made to take place for a fixed or adjustable length of time.

The same result obtained by reversing the pump 120, either automatically or manually, can be accomplished by opening the clamping mechanism of the pump so that portion B of the evacuation line 80 communicates with the exit 82 of the line. Since the resistance of the pump side of portion B of line 80 is smaller that at the opening of the instrument, the flow into B will take place from the pump side until equilibrium is reached between pressure in portion B of the evacuation line and the eye. The exit 82 of the outflow line must be above the level of the eye by a determined height to prevent syphoning.

Since it is not practical to have a pressure sensor in the eye it is impossible to define and keep track of its internal pressure at any and every particular instance during the operation. Thus, equilibrium between pressure in portion B of the evacuation line 80 and the eye is never really reached when the pump is turned backward. The accommodation of restoring pressure in portion B of the evacuation line should be to minimize and not eliminate entirely the flow form the eye after the flow is not desired or needed any longer, and the pump 120 is deactivated.

3. Reverse flow mode — This is obtained by the operator moving the control switch to another position, illustratively backwards on the foot switch. When this is done, the electrical controls are set up such that the direction of rotation of the instrument cutter motor is reversed and the evacuation mechanism 81 is stopped. Pressure valve 68 is closed and valve 69 is opened to set up the reverse pressure in line 70.

The high pressure flow of reverse flow fluid is supplied from bottle 60 to line 70 and to the opening 19 for the cutter in the instrument 10 to push away any material that might have clogged this opening or inadvertently entered the cutter opening.

A fourth mode of flow is created through the reverse flow line 70 after the evacuation process through line 80 is terminated. This equalizes the pressure on both sides of the evacuating port of the instrument which is in the operating field.

In accordance with the general principles of the invention, if desired, the infusion fluid can be supplied to the instrument over a separate supply line during the reverse flow mode and a separate pump can be used for the reverse flow mode. The separate pump and supply line can also have its own control circuit so that the pressure in the line will not be excessive.

The pressure in infusion bottle 60 also can be produced, maintained or changed by a system having a displacement type pump (e.g. a peristaltic or other suitable pump) for determining the amount of air pressed into the bottle or removed from it in order to maintain or regulate the desired pressure in the bottle at all stages of operation. This would be in response to control signals produced by the pressure transducer. A safety pressure valve is preferably used to prevent unwanted increases in pressure of the electronic circuit.

What is claimed is:

1. In combination, a system for use with a surgical instrument of the type having an operative portion at an operating site with the operative portion including selectively operable means for separating material from the object being operated on, a first means for delivering an infusion fluid to the operating site and a second means for removing separated material from the operating site,
    a source of infusion fluid,
    means including a single valve means for supplying infusion fluid from said source at variable pressure to said first means of said instrument,
    means producing a pressure differential condition at said second means of the instrument with respect to the pressure of the infusion fluid at said first means to provide removal of material from the operating site,
    and means for selectively operating said single valve of said infusion fluid supply means in first and second conditions wherein in the first condition when said means for separating material is inoperative to produce a lower pressure than when in said second condition when the means for separating material is operative.

2. The combination of claim 1 wherein said means for operating said infusion fluid supply means comprises servo means.

3. The combination of claim 2 wherein said servo means selectively operates to maintain a substantially constant difference in pressure between the first and second conditions.

4. The combination of claim 1 further comprising means including said single valve for supplying infusion fluid from said source to said second means, said means for selectively operating said infusion supply means operating in a third condition to produce a predetermined pressure for the infusion fluid supplied to said second means.

5. The combination of claim 4 wherein the pressure of the infusion fluid supplied to said second means is greater than the pressure of the infusion fluid supplied to said first means.

6. The combination of claim 1 further comprising means for setting the pressure of the infusion fluid to a reference level.

7. The combination of claim 4 further comprising means for setting the pressure of the infusion fluid supplied to both said first and second means to a reference level.

8. In combination, a system for use with a surgical instrument of the type having an operative portion at an operative site with the operative portion including first means with an outlet port for delivering an infusion fluid to the operating site and a second means including an inlet port for removing material from the operating site,
    a source of infusion fluid supplied to said first means,
    means in fluid communication with said second means for producing an evaucation pressure,
    transducer means for measuring the evacuation pressure,
    and means responsive to the spressure measured by said transducer means for terminating the evacuation when the evacuation pressure exceeds a predetermined limit.

9. The combination of claim 8 wherein said means for producing the evacuation pressure comprises a pump and said terminating means stops the pumping action of the pump.

10. The combination of claim 9 wherein the pump comprises a peristaltic pump.

* * * * *